United States Patent [19]

Wilkinson

[11] 3,933,919
[45] Jan. 20, 1976

[54] HYDROFORMYLATION OF MONO-α-OLEFINS AND MONO-α-ACETYLENES

[76] Inventor: Geoffrey Wilkinson, 6 Tennul Close, London W. 2, England

[22] Filed: Mar. 4, 1974

[21] Appl. No.: 447,827

Related U.S. Application Data

[60] Continuation of Ser. No. 821,521, Feb. 10, 1968, abandoned, Division of Ser. No. 541,118, Dec. 15, 1965, abandoned.

[30] Foreign Application Priority Data

Dec. 15, 1964 United Kingdom............... 50984/64
Feb. 16, 1965 United Kingdom................ 6676/65
Oct. 5, 1965 United Kingdom............... 42138/65

[52] U.S. Cl. ... 260/604 HF; 252/431 R; 252/431 N; 252/431 P; 260/497 R; 260/498; 260/409; 260/514 M; 260/523 R; 260/533 A; 260/598; 260/599; 260/605; 260/617 C; 260/618 H; 260/631 H; 260/632 CA; 260/632 HF; 260/631 S; 260/635 A; 260/669 QZ; 260/669 R; 260/677 H; 260/682; 260/683.9; 260/690

[51] Int. Cl.$^2$........................................ C07C 45/10
[58] Field of Search............................ 260/604 HF

[56] References Cited
FOREIGN PATENTS OR APPLICATIONS
1,459,643 10/1966 France....................... 260/604 HF OTHER PUBLICATIONS
Jondine et al., "Chem. and Industry," p. 560, (1965).
Osbom et al., "Chem. Comn.," No. 2, p. 17, (Jan. 1965).
Vallarmo, "J. Chem. Soc.," pp. 2287–2292, (1957).

*Primary Examiner*—Norman Morgenstern
*Attorney, Agent, or Firm*—Cushman, Darby & Cushman

[57] ABSTRACT

This invention relates to improvements in certain catalytic reactions, namely, hydrogenation, hydroformylation and carbonylation reactions.

3 Claims, No Drawings

HYDROFORMYLATION OF MONO-<-OLEFINS AND MONO-<-ACETYLENES

This is a continuation, of application Ser. No. 821,521, filed Dec. 10, 1968, which application is a divisional of Ser. No. 514,118, filed Dec. 15, 1965.

Hydrogenation reactions have hitherto mainly employed heterogeneous catalysts, particularly various forms of metallic nickel, platinum or palladium to promote the reaction, while hydroformylation and carbonylation reactions have usually involved the use as catalyst of dicobalt octacarbonyl. The use of all such catalysts often requires considerable reaction pressure and elevated temperature and in many instances the catalyst rapidly becomes poisoned, probably because if the catalyst is a solid the catalysis is due to a surface effect which becomes inhibited by the presence of impurities. Other heterogeneous catalysts such as copper chromite or mixed oxide catalysts have been employed for hydrogenation but they suffer from the need for frequent replenishment and, if practicable, regeneration of the spent catalyst for re-use. There has thus existed a need for a catalyst which enables the desired reactions to be carried out at temperatures and pressures that are no more then moderate and which is homogeneous with the reaction medium. These desiderata have, however, hitherto been largely unfulfilled.

In French patent specification No. 1,300,404, recently published, it is claimed that hydroformylation reactions may be carried out at moderate temperatures and pressures in the presence as catalyst of a complex containing in the molecule a transition metal having an atomic number from 23 to 32, 40 to 51 or 57 to 84 and at least one molecule of a biphyllic ligand containing trivalent phosphorus, arsenic or antimony. However, the experimental work described therein is limited to complexes formed from dicobalt octacarbonyl and a phosphine or arsine ligand and it can be shown that other complexes within the above generic definition are ineffective in promoting a hydroformylation reaction.

It has now been discovered that certain readily-prepared soluble halogen- or pseudo-halogen-containing complexes of platinum group metal halides or pseudo-halides are effective when employed in a homogeneous liquid reaction medium as catalysts both for the hydrogenation of unsaturated organic linkages and for the hydroformylation and carbonylation of olefins. These complexes are formed in part from a halide or pseudo-halide of a platinum group metal and are distinguished from the complexes described in French patent specification No. 1,300,404 by the fact that they contain at least one halogen or pseudo-halogen atom in the molecule of the complex; such complexes are hereinafter termed "halogen containing platinum group metal complexes". The term "halide" is used throughout this present specification to refer preferably to chlorides, bromides or iodides and "pseudo-halides" to refer to cyanides, cyanates and thiocyanates. The other moieties of the "halogen-containing platinum group metal" complexes with which the present invention is concerned are derived from an organic ligand which is an isocyanide or a compound having a coordinating atom which has a lone pair of electrons and which is of an element.

Accordingly, the invention provides a hydrogenation, hydroformylation or carbonylation process in which an unsaturated organic compound (as hereinafter defined) is reacted with hydrogen and/or carbon monoxide in the presence of a liquid medium which contains dissolved therein a catalytic quantity of a catalyst which is a halogen or pseudo-halogen-containing complex that has been formed from a halide or pseudo-halide of a platinum group metal and at least one ligand which is either: (a) an organic isocyanide; or (b) an organic compound having in its molecule an atom of an element selected from Groups VB or VIB of the Periodic Table, said atom possessing a long pair of electrons.

The platinum group metal may (except when otherwise specified) be ruthenium, rhodium, palladium, osmium, iridium or platinum and the halide may be any conveniently available halide or pseudo-halide thereof, usually the chloride, though the bromides and cyanides may be preferred in some instances. If desired, the halide or pseudo-halide may be in a hydrated form. The platinum group metal may be in any convenient oxidation state, but it may be in some instances that the metal becomes reduced to a lower valency state during the formation of the complex, some of the ligand or the solvent acting as a reducing agent.

The ligand for present use is defined as a compound which is either (a) an organic isocyanide or (b) an organic compound having in the molecule an atom of an element selected from Groups VB or VIB of the Periodic Table, that is usually a nitrogen, phosphorus, arsenic, sulphur or selenium atom, such atom being in such valency state that it possesses a lone pair of electrons. The preferred ligands within the definition of categories (a) and (b) include: tertiary amines, phosphines, arsines and stibines; tertiary phosphite esters; organic nitriles; and isocyanides; as well as sulphoxides, phosphine oxides, dialkyl sulphides and mercaptans. For example, there may be employed pyridine, quinoline or dimethylaniline, though more neutral compounds are preferred, such as for example, tributyl or triphenyl phosphine; trimethyl, tributyl or triphenyl phosphite; dimethylphenylarsine; triphenyl arsine or stibine; dibutyl sulphide; dimethyl sulphoxide; triphenyl phosphine oxide; phenyl isocyanide or acetonitrile. Also to be treated as organic compounds for present purposes are such ligands within category (b) as phosphorus triisocyanate and phosphorus triisothiocyanate.

The complex may be represented by the empirical formula $L_nM^vX_y$, where each L represents a ligand of the type hereinbefore described, M is the platinum group metal and each X represents a halogen atom or pseudo-halogen group and where $n$ is the number of ligand molecules present, $y$ is the number of halogen atoms and/or pseudo-halogen groups present and is at least one, and $v$ is the valency state of the metal M. It is preferred that the complex should be electronically neutral, so that $v = y$, but it may be a positively charged ion in which case $v$ can be greater than $y$. The preferred valency states of the platinum group metals in the complex depends on the metal employed. For ruthenium and osmium it is 2, 3 or 4; for rhodium it is 1 or 3; for iridium it is 1, 3 or 4; and for platinum and palladium it is 2 or 4. The complex normally has an octahedral structure, that is the sum of $n$ and $y$ is 6, when the metal and its valency is $Rh^{III}$, $Ir^{III}$, $Ru^{II}$, $Os^{II}$ or $Pt^{IV}$, though with ruthenium it may have a 5-coordinate quesi-octahedral structure. However, when the metal and its valency is $Rh^I$, $Pt^{II}$ or $Pd^{II}$, the complex is normally of tetragonal structure, that is the sum of $n$ and $y$ is 4. If desired, the complex solution may contain a little hydrogen chloride which in certain circumstances may promote the stability of the complex, for example when chloride ions are required for association with the complex when this is a cation.

A particularly effective species of catalyst for present use, particularly for use in the hydrogenation processes of the present invention, is one represented by the formula $(R_3Z)_3Rh'X$ where the donor ligand $R_3Z$ is a tertiary phosphine, arsine or stibine, that is a 1:3 molar complex of a rhodium-I halide and the specified donor ligand. Such complexes have not, it is believed, hitherto been reported and, therefore, constitute a further aspect of the present invention. These complexes of formula $(R_3Z)_3Rh'X$ may be prepared by refluxing an excess, for example from 3 to 10 times the stoichiometric quantity, of the tertiary phosphine with a rhodium trihalide in a solvent, preferably an alcoholic solvent, such as ethanol. On cooling the complex often crystallizes from the solution in a yield which is virtually quantitative. The crystals may be separated and washed to remove the excess phosphine which may adhere. Alternatively, the complexes may be made by using tertiary phosphines, arsines or stibines to displace other ligands from rhodium-I complexes. The preferred catalysts of this type have the formula $(R'_3P)_3Rh'X'$ wherein each R' represents an aryl group, preferably phenyl, and each X' represents a chlorine, bromine or iodine atom, preferably chlorine. The complexes of formula $(R_3Z)_3Rh'X$ are particularly effective as hydrogenation catalysts and at a hydrogen pressure of 1 atmosphere very rapidly effect reduction of olefinic and acetylenic compounds to the corresponding saturated compounds. At this hydrogen pressure they also more readily effect reduction of aldehydes to the corresponding primary alcohols than do the other catalysts specifically described herein. Furthermore, reduction of olefinic halogen compounds, such as allyl bromide, does not affect the halogen substituent, the product being the corresponding saturated halogen compound.

It is preferred to form the complex by mixing in the presence of a suitable solvent the platinum group halide or pseudo-halide and ligand molecules in substantially the appropriate stoichiometric proportions according to the molecular formula of the complex, bearing in mind that a calculated excess of the ligand may be necessary if it is also to serve as a reducing agent for the platinum group metal. For example, methods of preparation of some of the complexes are given in J. Chem. Soc. 1964, 2508–2513. The said liquid reaction medium conveniently comprises a lower alkanol, having up to about 4 carbon atoms, such as ethanol or methanol; ethers, such as diethyl ether or tetrahydrofuran are also suitable. Other suitable solvents and co-solvents include aliphatic and aromatic hydrocarbons, such as hexane and benzene. The stoichiometry of the complex formed is usually readily determined by conventional analytical procedures and in many cases the complex can be crystallized, if desired, from suitable concentrated solutions such as alcoholic solution.

Many of the ruthenium-containing complexes described generally above are particularly suitable for use in the hydrogenation reactions of the invention, but it has been found that these are often much less suitable for hydroformylation and carbonylation reactions. This appears to result from the fact that when many of the ruthenium-containing complexes are contacted with carbon monoxide an interaction occurs and the complex may become largely or completely insolubilized in the reaction mixture. The reaction mixture may then not contain the necessary soluble complex and accordingly the yield of product from a hydroformylation or carbonylation process using such a ruthenium complex is much reduced. It is therefore to be appreciated that, while the specified ruthenium-containing complexes are very effective as catalysts in the hydrogenation reaction of the invention, their use in the present hydroformylation and carbonylation processes is not particularly advocated since, due to insolubilization, there may be present in solution insufficient of the catalyst complex to permit a satisfactory yield from the process.

With the complexes described herein, particularly with the ruthenium complexes, the presence of an alcoholic solvent or cosolvent may enhance their activity. This appears to result from displacement of some, but not all, of the ligands from the complex and replacement thereof with one or more alcoholic solvent materials. The presence of such an alcoholic solvent or co-solvent, particularly a lower alkyl $(C_{1-4})$ monohydric alcohol in the reaction mixture is preferred.

If the reaction to be carried out is a hydrogenation reaction, in which case, of course, no carbon monoxide, is employed, the said "unsaturated organic compound" is one containing a multi-bond linkage from a carbon atom to another carbon atom or to an oxygen, sulphur or nitrogen atom. If the reaction to be carried out is a hydroformylation reaction involving reaction with both hydrogen and carbon monoxide or a carbonylation reaction involving reaction with carbon monoxide only the "unsaturated organic compound" is an olefinic compound, that is an ethylenically-unsaturated or acetylenically-unsaturated hydrocarbon or substituted hydrocarbon. The substituents present should be inert to the reaction and such substituents include, for example, halogen and hydroxyl substituents. Although not bound by an theory, the hydroformylation of acetylenic compounds, which as been found to occur with the catalyst described herein, may be considered as an initial hydrogenation to the corresponding ethylenically-unsaturated compound followed by hydroformylation of this so that the product is an aldehyde, or alcohol obtained by subsequent hydrogenation thereof.

Thus, by the hydrogenation process of the present invention: olefinic and acetylenic linkages may be hydrogenated; aldehydes, ketones or their thio-analogues reduced to the corresponding alcohols or thiols; or nitriles or Schiff's bases reduced to amines. In such hydrogenation reactions, the unsaturated reactant may contain any substituents which do not interfere with the course of the reaction, for example the reactant may contain cyclo-aliphatic, aryl or hydroxyl groups. The hydrogenation reaction of the invention is also particularly effective for the reduction of aldehydes and ketones to the corresponding alcohols, for example preparing heptanol from heptaldehyde, butanol-2 from methyl ethyl ketone, cyclohexanol from cyclohexanone; and for the hydrogenation of olefinic double bonds, for example the preparation of saturated fatty acids and their derivatives from the naturally-occurring unsaturated acids such as oleic, linoleic and ricinoleic acid, and the hydrogenation of terpenoid double bonds such as the production of methanol from isopulegol. Acetylenic compounds, e.g. phenyl acetylene and more particularly acetylenic alcohols, are also reduced, usually to a mixture of the corresponding alkene and alkane, with any hydroxyl group remaining as such in the product. Use of excess hydrogen results in the product being mainly the alkane at the expense of the alkene. It has also been found that acetylenic alcohols are more readily reduced than acetylenic hydrocarbons.

By the present hydroformylation reaction olefins or acetylenic hydrocarbons may be converted to aldehydes which may subsequently be reduced according to the hydrogenation process of the invention; and by the carbonylation reaction of the invention olefins or acetylenic hydrocarbons may be converted into carboxylic acids or, in the presence of alcohols, into esters thereof.

The hydroformylation reaction of the invention is particularly effective. In this an olefinic compound is reacted in the presence of a catalyst as defined with a mixture of hydrogen and carbon monoxide. Theoretically this mixture should be an equimolecular one, but it is normally preferably to have present an excess of carbon monoxide and a molar ratio of hydrogen: carbon monoxide of from 1:1 to 1:5 is normally employed. In this way the concurrent hydrogenation reaction is usually inhibited. The reaction temperature during hydroformylation is normally kept below 110°C, since the hydrogenation reaction appears to be favored above this. The temperature can be raised to 200°C. In some instances, the yield of resulting aldehyde appears to be virtually quantitative. Preferably, but not necessarily, the olefinic compound is an α-olefin, for example, ethylene, propylene, butene-1, hexene-1, octene-1, the higher α-olefins produced by the thermal cracking of paraffin wax and dienes such as butadiene (when normally only one of the double bonds reacts). As substituted olefinic compounds there may be employed, for example, allyl alcohol, methallyl alcohol, isopropenylbenzene, styrene, vinyl cyclohexene, cyclohexene or cyclooctene.

The aldehydes which result from the above-described hydroformylation reaction may conveniently be subjected to a subsequent hydrogenation reaction wherein the aldehydes are reduced, that is hydrogenated, to the corresponding primary alcohol; a little of the corresponding alkane usually results. In such hydrogenation reaction the same or different complex catalysts may be used as in the hydroformylation reaction, the hydrogenation reaction being thus, for example, conducted in a homogeneous reaction mixture under a hydrogen pressure of up to 60 atmospheres and at temperatures up to about 120°C. Such a two-step hydroformylation and subsequent hydrogenation process, particularly when the same complex catalyst is employed in each step, provides a convenient synthetic route for obtaining tridecyl alcohol from dodecant-1, nonanols from the corresponding octenes and n-heptanol from n-hexene-1. The two-step reaction using the complex as catalyst in each step is conveniently carried out as a single reaction sequence making use of higher reaction temperatures, for example 90° to 120°C. and more prolonged reaction duration so that the hydrogenation reaction can occur in the same reaction zone after that of hydroformylation.

The carbonylation process of the invention is conducted in similar fashion to the hydroformylation reaction though the hydrogen reactant is, of course, not present. The product is a carboxylic acid unless an alcohol solvent, such as ethanol, is employed when the resulting product may be the alkyl ester of the carboxylic acid primary reaction product. In general, the preferred olefins for use in the hydroformylation reaction are also the preferred olefins for use in the carbonylation reaction and the invention therefore provides a convenient process for the production of, for example, heptoic acid (from hexene-1) and cyclohexanecarboxylic acid (from cyclo-hexene) or ester derivatives thereof.

The hydroformylation and carbonylation reactions primarily result in the product formed by α-addition of the elements of formaldehyde or formic acid respectively to the olefinic bond, i.e. anti-Markownikow addition. However, a little β-addition also occurs so that the product is usually a mixture of isomeric aldehydes or acids, but this is often no real disadvantage as the mixture can often be used as such, for example in making alcohols for use in the production of plasticizers or acids for use in paint driers where mixed compounds are not disadvantageous; or alternatively the mixture can be separated.

The process is carried out in a liquid reaction medium which usually comprises a solvent or co-solvent for the catalytic complex but may be contributed by the unsaturated organic compound reactant, or as the reaction proceeds, the resulting product. The complex must be dissolved in the liquid reaction medium. The reaction is preferably conducted at moderately elevated temperatures and pressures, for example, temperatures of 50° – 150°C., particularly 60° – 100°C., and pressures of 5 to 100 atmospheres are very suitable. The conditions shall be such that the reaction mixture remains liquid throughout the reaction and autogenous pressure is therefore conveniently employed. The progress of the reaction can be followed in the normal way by observing the consumption of hydrogen and/or carbon monoxide.

The amount of catalyst present does not appear to be critical but an amount of from 0.1 to 5.0 percent, preferably 0.5 to 3 percent, by weight based on the weight of the unsaturated compound is normally employed.

When reaction is complete the product is separated from the reaction mixture, usually by fractional distillation. This may, if necessary, conveniently be carried out under reduced pressure. The separation is preferably not carried out to the extent that all the solvent is removed from the involatile complex. The distillation "heel" comprising the residual catalyst may then be passed for re-use in a further process of the invention, often after the addition to it of a further quantity of solvent. Since separation of the product from excess pyridine may not be too easily accomplished, pyridine is for this reason less desired for forming the complex for present use.

The invention is now illustrated by the following examples.

EXAMPLE 1 n-Hexane from hexene-1.

A complex of formula $(Ph_3P)_3RhCl_3$ was pre-formed by mixing three molecular proportions of triphenyl phosphine with one molecular proportion of rhodium trichloride in ethanol. To this complex (0.25 g) dissolved in ethanol (30 ml) was added benzene (20 ml) and hexene-1 (10 ml). Hydrogen was passed into the solution and the complex maintained in a closed vessel at 25°C. for 20 hours while the gauge pressure was 0.5 atmosphere. Distillation of the reaction mixture gave n-hexane in 95 percent yield.

EXAMPLE 2 n-Heptanol from n-heptaldehyde.

To the complex (0.1 g) prepared in Example 1 dissolved in ethanol (2 ml) was added benzene (2 ml) and n-heptaldehyde (3 ml). Hydrogen was passed into the solution of the complex maintained in a closed vessel at 110°C. for 12 hours with a gauge pressure of 60 atmospheres. Distillation of the reaction mixture gave n-heptanol in 95 percent yield.

EXAMPLE 3

Hydrogenation of hexyne-1.

A complex of formula $(Ph_3As)_3RhCl_3$ was formed by mixing triphenylarsine (3 mols. and rhodium trichloride (1 mole) in ethanol followed by crystallization of the complex from the solution. This complex (4 mg.) was dissolved in benzene (4 ml) to which hexyne-1 (3.2 g.) was added. To this mixture in an autoclave at room temperature hydrogen was admitted at 65 atmospheres for 12 hours. Distillation of the resulting mixture yielded a quantitative yield of n-hexane.

EXAMPLE 4

Hydroformylation of hexene-1.

To the complex (0.15 g) prepared as in Example 1 dissolved in a mixture of ethanol (2 ml) and benzene (2 ml) was added hexene-1 (4 ml). With the reaction mixture in an autoclave, hydrogen and carbon monoxide were separately passed in at gauge pressures of 40 and 50 atmospheres respectively during 12 hours while the temperature of the reaction mixture was maintained at 55°C. Subsequent distillation of the reaction mixture gave n-heptaldehyde in 70 percent yield and 2-methylcaproic aldehyde in 15 percent yield, the latter compound arising from β-addition of the elements of formaldehyde in the hydroformylation reaction.

EXAMPLE 5

Hydroformylation of hexene-1.

A complex of formula $(Ph_3As)_2PtCl_2$ was formed by mixing and crystallizing in ethanol triphenylarsine (3 mols.) and platinic chloride $(PtCl_4)$. This complex (100 mg.) was dissolved in benzene (4 ml) and hexene-1 (3.2 g) added. This mixture was heated in an autoclave for 12 hours at 70°C. under a hydrogen pressure of 40 atmospheres and a carbon monoxide pressure of 45 atmospheres. Fractional distillation of the resulting mixture yielded n-heptaldehyde and 2-methyl caproic aldehyde.

EXAMPLE 6

Hydroformylation of hexene-1.

A complex of formula $[(Ph_2EtP)_cRu_2Cl_3]Cl$ was crystallized from a mixture in ethanol of ethyldiphenylphosphine (4 mols.) and ruthenium trichloride (1 mol.). To a mixture of this complex (50 mg.) dissolved in ethanol (2 ml.) was added hexene-1 (4 ml.) at 70°C. under a hydrogen pressure of 40 atmospheres and a carbon monoxide pressure of 40 atmospheres. Distillation of the resulting mixture yielded n-heptaldehyde and 2-methyl caproic aldehyde.

EXAMPLE 7

Hydrogenation of acetylenic compounds.

A (1:1) molar complex of triphenyl phosphine and rhodium trichloride was prepared as catalyst by suspending finely ground rhodium trichloride trihydrate (2.0 g.) and triphenyl phosphine (12 g.) in methanol (40 ml.) and stirring the mixture at room temperature for 90 minutes, after which the formed brown precipitate of the complex was filtered off and washed with ethanol (50 ml.) and diethyl ether (50 ml.) to remove unchanged reactants; no further purification was necessary.

The catalyst (0.25 g.) was dissolved in benzene (25 ml.) at 30° – 50°C. and ethanol (25 ml.) added, followed by the acetylenic compound (0.1 mol) as specified below. The solution was deaerated by a stream of nitrogen and hydrogen admitted to the reaction system at a total pressure of about 50 cm. mercury while the mixture was agitated. After about 12 hours no further absorption of hydrogen occurred. The resulting mixture was analyzed chromatographically and it was found the acetylenic compound had been reduced to a mixture of the corresponding olefinic and saturated hydrocarbons. The reaction mixture could be separated by fractional distillation.

Many acetylenic compounds were subjected to the above procedure. It was found that they were reduced in the following order of decreasing rapidity:

3-methylbut-1-yne-3-ol;
3-methylpent-1-yne-3-ol;
hex-1-yne;
1-ethynylcyclohexan-1-ol;
pent-2-yn-1,5-diol; and
acetylene.

It was also found that higher pressure of hydrogen could be conveniently used, for example, at pressures of 50–100 atmospheres and that when excess hydrogen was present the final reduced product was substantially the saturated hydrocarbon.

EXAMPLE 8

Hydroformylation of hexyne-1.

The catalyst as prepared in Example 7 (0.1 g.) was dissolved in benzene (4 ml.) and hexyne-1 (4 ml.) was added. The solution was placed in a small autoclave which was filled with a mixture of hydrogen and carbon monoxide (molar ratio 1:4) at a total pressure of 120 atmospheres. After 16 hours at 110°C. reaction was complete. From the product there was isolated n-heptaldehyde (yield 10 percent) and 2-methylhexaldehyde (yield 10 percent).

EXAMPLE 9

Reduction of hexene-1 with $(Ph_3P)_3Rh^ICl$ catalyst.

Triphenyl phosphine and rhodium trichloride in approximately 5:1 molar ratio were refluxed in ethanol for 2–3 hours. On cooling purple crystals of the complex $(Ph_3P)_3Rh^ICl$ were obtained in virtually quantitative yield based on the rhodium value. The crystals were separated, washed with a little cold ethanol to remove excess triphenyl phosphine and dried.

The catalyst (0.25 g.) was dissolved in benzene (25 mol.) and ethanol (25 ml.) and hexene-1 (5 ml.) added to the mixture. The solution was deaerated by evacuation and hydrogen admitted to the system at a pressure of 50 cm. mercury. A smooth take-up of hydrogen was observed and was virtually complete after 2 hours at 20°C. The resulting solution was shown to contain n-hexane.

EXAMPLE 10

Reduction of allyl bromide with $(Ph_3P)_3Rh^ICl$ catalyst.

The procedure of Example 9 was repeated but using allyl bromide (12.1 g.) instead of the hexene-1. Uptake of hydrogen was complete after 6 hours at 20°C. and the resulting solution was shown to contain 1-bromopropane.

EXAMPLES 11–16

Hydrogenations with ruthenium-containing complexes.

A solution of a complex of formula as stated in Table 1 below in a mixture of ethanol and benzene using the amounts there specified was placed in a stainless steel autoclave together with hexene-1 (4 ml.). The autoclave was then charged with hydrogen to the stated pressure and after the stated period at room temperature the contents of the autoclave were analyzed and the percentage of hexene-1 which had been hydrogenated to hexane was determined, the results being given in the said Table 1.

TABLE 1

| Example | Formula of Complex | Amount of Complex (g.) | Solvent Ethanol (ml) | Solvent Benzene (ml) | Hydrogen Pressure (atmos.) | Reaction Time (hours) | Conversion (per cent) |
|---|---|---|---|---|---|---|---|
| 11 | $Ru(Ph_3P)_2Cl_2.MeOH$ (a) | 0.1 | 2 | 2 | 55 | 15 | 70 |
| 12 | $[Ru(Ph_2EtP)_6Cl_3]Cl$ (b) | 0.1 | 3 | 3 | 90 | 15 | 90 |
| 13 | $Ru(Ph_3P)_3Cl_3$ | 0.05 | 2 | 2 | 60 | 18 | 95 |
| 14 | $Ru(Ph_3P)_4Cl_2$ | 0.1 | 4 | 2 | 80 | 15 | 100 |
| 15 | $Ru(Ph_2PCH_2CH_2PPh_2)_2Cl_2$ (b) | 0.05 | 2 | 2 | 60 | 18 | 65 |
| 16 | $Ru(Ph_3As)_2Cl_3.MeOH$ | 0.05 | 2 | 2 | 70 | 15 | 60 |

(a) Complex prepared according to the procedure of Vasko (Chem. and Ind., 1961, 1402)
(b) Complex prepared according to the procedure of Chatt and Hayter (J. Chem. Soc., 1961, 896)

EXAMPLES 17–21

Hydroformylation with ruthenium-containing complexes.

These examples illustrate the reduced yields of product that are obtained when certain ruthenium complexes are employed in hydro-formylation reactions. The reduced yield is due to the marked insolubilization in the reaction medium of the complex after treatment with carbon monoxide.

The same apparatus and general procedure was employed as in Examples 11–16 but the autoclave was charged with both hydrogen and carbon monoxide and was heated during the reaction. In each example a solution of the stated complex (0.05 g.) in a 1:1 mixture of ethanol and benzene (4 ml.) and hexene-1 (4 ml.) were employed. Details of the complex, gas pressures, temperatures and reaction time employed are given in Table II below. In each instance some insolubilization of the complex in the reaction mixture was noted and though hydroformylation of the hexene-1 to a mixture of n-heptaldehyde and 2-methylhexaldehyde was observed, the yields were not high; further reduction of these aldehydes to the corresponding alcohols were not observed under the reaction conditions employed.

TABLE II

| Example | Formula of Complex | Gas Pressure (Atmos.) Hydrogen | Gas Pressure (Atmos.) Carbon Monoxide | Reaction Time (hours) | Reaction Temperature (°C.) | Total Yield of Aldehydes (per cent) |
|---|---|---|---|---|---|---|
| 17 | $[Ru(PhEt_2P)_6Cl_3]Cl$ | 40 | 40 | 30 | 70 | 20 |
| 18 | $Ru(Ph_3P)_2Cl_3.MeOH$ | 30 | 80 | 15 | 110 | 25 |
| 19 | $Ru(Ph_3P)_3Cl_3$ | 35 | 50 | 18 | 110 | 10 |
| 20 | $Ru(Ph_3P)_4Cl_2$ | 35 | 80 | 18 | 110 | 5 |

In summary, there are five major embodiments of this invention:
1. New catalytic compounds,
2. A method for the preparation of the new compounds,
3. A novel hydrogenation reaction,
4. A novel hydroformylation reaction, and
5. A novel carbonylation reaction.

Turning to the new compounds, a preferred type is represented by the formula

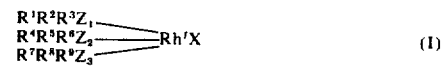
(I)

In this formula $R^1$–$R^9$ inclusive are organic radicals, preferably aryl having from 6 to about 10 carbon atoms. By "aryl" is meant a radical embodying a benzenoid nucleus. Typical radicals of this type are phenyl, tolyl (including the o, m and p radicals), xylyl (all isomers), mesityl, durenyl, butylphenyl, etc.

$Z_1$–$Z_3$, inclusive, in the above formula are phosphorus, arsenic or antimony atoms; preferably phosphorus or arsenic, and most preferably phosphorus.

X in the above formula is a halogenoid moiety selected from the class consisting of chlorine, bromine and iodine, and pseudo-halogen groups selected from cyanide, cyanate and thiocyanate.

It is immediately apparent to a skilled practitioner that the novel compounds represented by the above generic formula may have as many as 9 aryl groups and as many as three Group VB elements. Preferably, the three organic radicals bonded to each Group VB element are the same. More preferably, all 9 organic radicals bonded to the Group VB elements are identical. In a most preferred embodiment all three Group VB elements in these compounds are the same.

Thus, a most preferred embodiment of this invention encompasses compounds having the formula $$(R_3Z)_3RhX \quad (II)$$

wherein R is an aryl radical having from 6 to 10 carbon atoms, Z is a Group VB element having an atomic number of at least 15 and not more than 51, and X is a halogen atom having an atomic number of at least 17 and not more than 53. Of the halogen atoms, chlorine (atomic number 17), is especially preferred.

An important feature of this invention is that the rhodium atoms within the novel compounds above described are in the uni-positive valence state. Another important feature is that these novel compounds are useful as catalysts for hydrogenation, hydro-formylation and carbonylation reactions as described above and summarized below.

As mentioned above, the preparation of the novel compounds of this invention is a major embodiment of this invention. The process is readily carried out, it being only necessary to contact the ligand molecule to be contained in the catalytic complex with the metal halide or pseudo-halide reactant. When preparing the novel complexes defined by formulas I or II above, it is only necessary to contact a phosphine, arsine, stibine or mixture thereof with a rhodium halide or pseudo-halide wherein the rhodium is in the tripositive state. For the complex having a unipositive rhodium atom to occur, a reduction of rhodium must take place when a trivalent rhodium salt is used as a reactant, hence a material to be oxidized must be present in the reaction system. The material to be oxidized can be an excess of the phosphine, arsine or stibine reactant. In other words, the reaction of an excess of phosphine, arsine, stibine or mixture thereof with a rhodium(III)halide or pseudo-halide yields a compound of Formula I or II. Thus, more than three to about 10 moles of phosphine, arsine or stibine are used for each mole of rhodium-(III)halide or pseudo-halide employed. As stated above, the process is preferably carried out in a solvent such as a lower alkanol.

The reaction temperature is not critical. Preferred reaction temperatures are those which give an acceptable reaction rate and are not so high as to have a deleterious effect on the products or the reactants. Mild temperatures, e.g. those within the range of from about −5° to about 100°C. can be used. However, temperatures within the range of from about 40° to about 85°C. are preferably employed.

The reaction pressure is not critical and the process for the preparation of the compound of this invention proceeds well under ambient pressures. Usually pressures less than atmospheric offer no material advantage, but they can be used if desired. Pressures above atmospheric, e.g., up to about 50 or 100 atmospheres, can be used. These elevated pressures are especially efficacious when it is desired to use a reaction temperature which is above the normal boiling point of the solvent employed.

The reaction time is not a truly independent variable and it depends to some extent on the inherent reactivity of the reactants employed and other process conditions used. In most instances, a reaction temperature in the order of from one minute to 24 hours is sufficient. Preferred times are less than ten hours.

The reaction can be carried out under a blanket of an inert gas. However, it is not necessary to do so. Nitrogen is the cheapest and most readily available inert gas and, therefore, it is preferred. However, argon, xenon and the other rare gases may be used if desired.

The following example, where all parts are by weight, further illustrates the formation of the compounds of this invention.

EXAMPLE 21

Triphenylphosphine (which was freshly recrystallized from ethanol), 12 parts, was dissolved in about 280 parts of hot ethanol. Another solution consisting of 56 parts of hot ethanol and two parts of rhodium trichloride trihydrate was also prepared. The two solutions were mixed and the resultant reaction mixture refluxed for 30 minutes. The hot solution was filtered and burgundy-red crystals were obtained. The crystals were obtained. The crystals were washed with two portions of 35 parts of diethylether and then dried in vacuum.

The crystals were the product, tris(triphenylphosphine) rhodium(I)chloride, m.p. 157°–158°C. Analysis indicated: C, 70.1; H, 4.9; Cl, 4.3. $C_{56}H_{45}ClP_3Rh$ requires: C, 70.1; H, 4.9; Cl, 3.8. The total yield of product isolated was 6.25 parts, i.e., 85 percent based on rhodium.

If more concentrated solutions are used; that is, 160 parts or less of ethanol in total, orange crystals of the product rhodium complex are obtained at once on refluxing. On continued refluxing, gradual conversion of these orange crystals to the normal deep red form occurs.

In a similar manner, a reaction of two moles of triphenylphosphine, two moles of triphenylarsine, and two moles of triphenylstibine with one mole of rhodium trichloride yields a mixture of tris(triphenylphosphine)rhodium(I)chloride, tris(triphenylarsine)-rhodium(I)chloride, tris(triphenylstibine)rhodium(I)chloride, triphenylphosphine bis(triphenylarsine)rhodium(I)chloride, triphenylarsine bis(triphenylphosphine)rhodium(I)chloride, triphenylarsine bis(triphenylstibine)rhodium(I)chloride, triphenylstibine bis(triphenylstibine)rhodium(I)chloride, triphenylstibine bis(triphenylarsine)rhodium(I)chloride, triphenylstibine bis(triphenylphosphine)-rhodium(I)chloride, (triphenylphosphine)(triphenylarsine)(triphenylstibine)rhodium(I)chloride and triphenylphosphine bis(triphenylstibine)rhodium(I)chloride. Similar bromine compounds are prepared by using rhodium tribromide in place of rhodium trichloride.

Three major embodiments of this invention are new hydrogenation, hydroformylation and carbonylation processes. In other words, this invention encompasses the reaction of an unsaturated organic compound having a multi-bond linkage with (a) hydrogen, (b) hydrogen and carbon monoxide and (c) carbon dioxide, in the presence of a liquid reaction medium having dissolved therein a catalytic quantity of a catalyst having the formula $L_nM^vX_y$, wherein L is a ligand molecule having a donor atom selected from the class consisting of nitrogen, phosphorus, arsenic and antimony, said donor atom having a pair of electrons available for donation to metal atom M; $n$ is the number of ligand molecules present and is a positive integer having a value of at least one and less than 4; M is a metal atom selected from the class consisting of ruthenium, osmium, rhodium, iridium, palladium and platinum, $v$ is the valence of said metal atom and is a positive integer having a value of from 1 to 4; X is a halogenoid moiety selected from the class consisting of halogen atoms and pseudo-halogen groups; $y$ is the number of halogenoid moieties present and is an integer having a value of from 1 to 3.

The hydrogenation process of this invention can be used to add hydrogen to multiple bonds in polymers such as olefinic bonds in rubber and latex. Furthermore, other compounds can be hydrogenated according to the process of this invention as described above.

In general, stable unsaturated organic compounds are useful in the hydrogenation, hydroformylation and carbonylation processes of this invention. The unsaturated compounds are stable if the radicals bonded to the atoms connected by the multiple bond reacted in the process are not detrimentally altered during the course of the reaction. Furthermore, compounds having isolated multiple bonds are also preferred. A multiple bond is isolated if it is not in such juxtaposition with other groups or radicals in the molecule so that the reactivity of the multiple bond is materially altered by a chemical effect or steric hindrance. The unsaturated compounds may have non-hydrocarbon substituents appended to the radicals bonded to the atoms connected by the multiple bond. Preferably, these non-hydrocarbon substituents are unaltered during the process, e.g., hydroxy or halogen radicals. Preferably, the unsaturated compounds have up to about 24 carbon atoms. More preferably the radicals bonded to the atoms connected by the multiple bond are hydrocarbon radicals, that is, they are solely composed of carbon and hydrogen. In a preferred embodiment the multiple bond to be reacted is at the end of a chain, e.g., aldehydes having the formula R—CHO wherein R is a hydrocarbon radical. However, the multiple bond may be within a chain. Thus, alpha as well as internal olefins and acctylenes can be reacted. Both straight and branched chain compounds can be employed. However, straight chain compounds are preferred.

I claim:

1. A hydroformylation process comprising reacting hydrogen and carbon monoxide with a mono-$\alpha$-olefinically or mono-$\alpha$-acetylenically unsaturated aliphatic hydrocarbon, said process being carried out at a temperature in the range of 50°–150° C at a pressure of 5 to 100 atmospheres and in the presence of a liquid reaction medium having dissolved therein a catalytic quantity of a catalyst having the formula $L_nM^vX_y$, wherein L is a ligand molecule having a donor atom selected from the class consisting of phosphorus and arsenic, said donor atom having a pair of electrons available for donation to metal atom M; $n$ is the number of ligand molecules present and is a positive integer having a value of at least one and less than 4; M is a metal atom selected from the class consisting of ruthenium, osmium, rhodium, iridium, palladium and platinum, $v$ is the valency state of said metal atom and is a positive integer having a value of from 1 to 4; X is a halogenoid moiety selected from the class consisting of halogen, cyanide, cyanate and thiocyanate; Y is the number of halogenoid moieties present and is an integer having a value of from 1 to 3.

2. A process of claim 1 wherein said unsaturated organic compound is hexene-1, and said catalyst is defined as follows:

L is triphenylphosphine,
$n$ is equal to 3,
M is rhodium,
$v$ is equal to 1,
X is chlorine, and
$y$ is equal to 1.

3. The process of claim 1 wherein the hydrocarbon is hexene-1 or hex-1-yne.

* * * * *